US011471708B2

(12) United States Patent
Ruegg et al.

(10) Patent No.: US 11,471,708 B2
(45) Date of Patent: Oct. 18, 2022

(54) INJECTABLE BOTULINUM TOXIN FORMULATIONS

(71) Applicant: REVANCE THERAPEUTICS, INC., Newark, CA (US)

(72) Inventors: Curtis L. Ruegg, Redwood City, CA (US); Hongran Fan Stone, Menlo Park, CA (US); Jacob M. Waugh, Palo Alto, CA (US)

(73) Assignee: Revance Therapeutics, Inc., Newark, CA (US)

(*) Notice: Subject to any disclaimer, the term of this patent is extended or adjusted under 35 U.S.C. 154(b) by 0 days.

(21) Appl. No.: 16/656,115

(22) Filed: Oct. 17, 2019

(65) Prior Publication Data

US 2020/0215357 A1    Jul. 9, 2020

Related U.S. Application Data

(62) Division of application No. 15/937,388, filed on Mar. 27, 2018, now abandoned, which is a division of application No. 13/141,935, filed as application No. PCT/US2009/069576 on Dec. 28, 2009, now Pat. No. 9,956,435.

(60) Provisional application No. 61/142,063, filed on Dec. 31, 2008.

(51) Int. Cl.
| | | |
|---|---|---|
| *A61Q 19/08* | (2006.01) | |
| *A61K 8/64* | (2006.01) | |
| *A61K 39/08* | (2006.01) | |
| *A61K 8/02* | (2006.01) | |

(52) U.S. Cl.
CPC .......... *A61Q 19/08* (2013.01); *A61K 8/64* (2013.01); *A61K 2800/592* (2013.01); *A61K 2800/91* (2013.01)

(58) Field of Classification Search
CPC .................................................. A61Q 19/08
See application file for complete search history.

(56) References Cited

U.S. PATENT DOCUMENTS

| | | |
|---|---|---|
| 5,512,547 A | 4/1996 | Johnson et al. |
| 5,733,873 A | 3/1998 | Osterberg et al. |
| 5,756,468 A | 3/1998 | Johnson et al. |
| 5,804,604 A | 9/1998 | Frankel et al. |
| 5,877,278 A | 3/1999 | Zuckerman et al. |
| 6,358,917 B1 | 3/2002 | Carruthers et al. |
| 6,544,548 B1 | 4/2003 | Siller-Jackson et al. |
| 6,585,993 B2 | 7/2003 | Donovan et al. |
| 6,787,517 B1 | 9/2004 | Gil et al. |
| 6,844,324 B1 | 1/2005 | Zhang et al. |
| 6,962,703 B2 | 11/2005 | Foster et al. |
| 7,211,261 B1 | 5/2007 | Moyer et al. |
| 7,579,010 B2 | 8/2009 | Hunt |
| 7,727,537 B2 | 6/2010 | Modi |
| 7,780,967 B2 | 8/2010 | Hunt |
| 7,807,780 B2 | 10/2010 | Waugh et al. |
| 7,838,011 B2 | 11/2010 | Modi |
| 7,956,028 B2 | 6/2011 | Garigapati et al. |
| 8,092,788 B2 | 1/2012 | Dake et al. |
| 8,119,109 B2 | 2/2012 | Tamarkin et al. |
| 8,398,997 B2 | 3/2013 | Dake et al. |
| 8,404,249 B2 | 3/2013 | Dake et al. |
| 8,501,195 B2 | 8/2013 | Turkel et al. |
| 8,518,414 B2 | 8/2013 | Waugh |
| 8,568,740 B2 | 10/2013 | Waugh |
| 8,580,250 B2 | 11/2013 | Hunt |
| 8,623,811 B2 | 1/2014 | Stone et al. |
| 8,895,506 B2 | 11/2014 | Garigapati et al. |
| 8,920,795 B2 | 12/2014 | Jung et al. |
| 8,921,322 B2 | 12/2014 | Favre et al. |
| 8,974,774 B2 | 3/2015 | Dake et al. |
| 9,107,815 B2 | 8/2015 | Hunt |
| 9,125,804 B2 | 9/2015 | Webb et al. |
| 9,173,944 B2 | 11/2015 | Taylor et al. |
| 9,180,081 B2 | 11/2015 | Dake et al. |
| 9,198,856 B2 | 12/2015 | Burger et al. |
| 9,198,958 B2 | 12/2015 | Jung et al. |
| 9,211,248 B2 | 12/2015 | Dake et al. |
| 9,265,725 B2 | 2/2016 | Tamarkin et al. |
| 9,340,587 B2 | 3/2016 | Thompson et al. |

(Continued)

FOREIGN PATENT DOCUMENTS

| | | |
|---|---|---|
| CN | 1950100 A | 4/2007 |
| CN | 101228187 A | 7/2008 |

(Continued)

OTHER PUBLICATIONS

"Revance Reports Results for RT001 Topical Phase 3 Trial for Lateral Canthal Lines", Jun. 13, 2016, 5 pages.
Akers, M.J., "Excipient-Drug Interactions in Parenteral Formulations", Journal of Pharmaceutical Sciences, vol. 91, No. 11, Nov. 1, 2002, pp. 2283-2300.
Brandt, et al., "Efficacy and Safety Evaluation of a Novel Botulinum Toxin Topical Gel for the Treatment of Moderate to Severe Lateral Canthal Lines", Dermatologic Surgery, vol. 36, Dec. 2010, pp. 2111-2118.
English Translation of Notification for Reasons for Refusal issued in Japanese Patent Application No. JP2012517802, dated Jul. 10, 2014. 5 pages.

(Continued)

*Primary Examiner* — Gary B Nickol
*Assistant Examiner* — Lakia J Jackson-Tongue
(74) *Attorney, Agent, or Firm* — Ballard Spahr LLP

(57) ABSTRACT

This invention provides novel injectable compositions comprising botulinum toxin that may be administered to a subject for various therapeutic, aesthetic and/or cosmetic purposes. The injectable compositions contemplated by the invention exhibit one or more advantages over conventional botulinum toxin formulations, including reduced antigenicity, a reduced tendency to undergo unwanted localized diffusion following injection, increased duration of clinical efficacy or enhanced potency relative, faster onset of clinical efficacy, and/or improved stability.

13 Claims, 3 Drawing Sheets

Specification includes a Sequence Listing.

(56) References Cited

U.S. PATENT DOCUMENTS

| | | | |
|---|---|---|---|
| 9,469,849 | B2 | 10/2016 | Ruegg |
| 9,757,329 | B2 | 9/2017 | Webb et al. |
| 10,105,421 | B2 | 10/2018 | Taylor |
| 10,549,042 | B2 | 2/2020 | Vogt |
| 2002/0028216 | A1 | 3/2002 | Donovan |
| 2002/0197278 | A1 | 12/2002 | Allison |
| 2003/0118598 | A1 | 6/2003 | Hunt |
| 2003/0138437 | A1 | 7/2003 | Hunt |
| 2003/0147921 | A1 | 8/2003 | Goodnough et al. |
| 2003/0215412 | A1* | 11/2003 | Waugh ............... A61K 49/085 424/70.14 |
| 2003/0224020 | A1 | 12/2003 | Zabudkin et al. |
| 2003/0229034 | A1 | 12/2003 | Waugh et al. |
| 2004/0033241 | A1 | 2/2004 | Donovan |
| 2004/0086532 | A1 | 5/2004 | Donovan |
| 2004/0220100 | A1* | 11/2004 | Waugh ............... A61K 49/0054 514/44 R |
| 2005/0196414 | A1 | 8/2005 | Dake et al. |
| 2005/0214278 | A1 | 9/2005 | Kakuta et al. |
| 2005/0238669 | A1* | 10/2005 | Xiang ............... C12N 1/20 424/239.1 |
| 2006/0182767 | A1 | 8/2006 | Borodic |
| 2006/0210614 | A1* | 9/2006 | Quay ............... A61K 9/0073 424/448 |
| 2007/0037252 | A1 | 2/2007 | Dake et al. |
| 2007/0077259 | A1 | 4/2007 | Dake et al. |
| 2007/0134199 | A1 | 6/2007 | Frevert |
| 2007/0196364 | A1 | 8/2007 | Krishnamurthy et al. |
| 2008/0038203 | A1 | 2/2008 | Dake et al. |
| 2008/0050352 | A1 | 2/2008 | Webb et al. |
| 2008/0069841 | A1 | 3/2008 | Panjwani et al. |
| 2008/0102090 | A1 | 5/2008 | Panjwani et al. |
| 2008/0107690 | A1 | 5/2008 | Dake et al. |
| 2008/0200373 | A1 | 8/2008 | Waugh et al. |
| 2008/0233152 | A1 | 9/2008 | Waugh et al. |
| 2009/0010965 | A1 | 1/2009 | Eisele et al. |
| 2009/0028906 | A1 | 1/2009 | Grein et al. |
| 2010/0168023 | A1 | 7/2010 | Ruegg et al. |
| 2010/0196445 | A1* | 8/2010 | David ............... A61M 37/0015 424/443 |
| 2010/0215591 | A1 | 8/2010 | Stone et al. |
| 2011/0020229 | A1 | 1/2011 | Waugh et al. |
| 2011/0237506 | A1 | 9/2011 | Gar7igapati et al. |
| 2012/0107361 | A1 | 5/2012 | Thompson et al. |
| 2012/0238969 | A1 | 9/2012 | Ruegg et al. |
| 2012/0294844 | A1 | 11/2012 | Waugh et al. |
| 2013/0202636 | A1 | 8/2013 | Dake et al. |
| 2013/0224248 | A1 | 8/2013 | Taylor et al. |
| 2013/0224268 | A1 | 8/2013 | Alam et al. |
| 2014/0086900 | A1 | 3/2014 | Jung et al. |
| 2014/0099342 | A1 | 4/2014 | Edelson et al. |
| 2015/0064166 | A1 | 3/2015 | Jung et al. |
| 2015/0320781 | A1 | 11/2015 | Dake et al. |
| 2015/0322419 | A1 | 11/2015 | Ruegg |
| 2015/0328293 | A1 | 11/2015 | Webb et al. |
| 2016/0051646 | A1 | 2/2016 | Dake et al. |
| 2016/0089442 | A1 | 3/2016 | Jung et al. |
| 2016/0114014 | A1 | 4/2016 | Dake et al. |
| 2016/0184413 | A1 | 6/2016 | Taylor et al. |
| 2019/0183988 | A1 | 6/2019 | Jarstad et al. |

FOREIGN PATENT DOCUMENTS

| | | |
|---|---|---|
| CN | 101171018 B | 3/2013 |
| EP | 1488803 A1 | 12/2004 |
| GB | 2416122 A | 1/2006 |
| GB | 2419526 A | 5/2006 |
| JP | 2009511485 A | 3/2009 |
| KR | 20080016992 A | 7/2008 |
| RU | 2206337 C1 | 6/2003 |
| WO | 1996011699 A1 | 4/1996 |
| WO | 1997035604 A1 | 10/1997 |
| WO | 1999037326 A1 | 7/1999 |
| WO | 2001037656 A2 | 5/2001 |
| WO | 2001058472 A2 | 8/2001 |
| WO | 200207773 A2 | 1/2002 |
| WO | 2004006954 A2 | 1/2004 |
| WO | 2004019905 A1 | 3/2004 |
| WO | 2004043430 A2 | 3/2004 |
| WO | 2005007185 A2 | 1/2005 |
| WO | 2005084361 A2 | 9/2005 |
| WO | 2005084410 A2 | 9/2005 |
| WO | 2006013357 A1 | 2/2006 |
| WO | 2006013370 A1 | 2/2006 |
| WO | 2006094193 A2 | 9/2006 |
| WO | 2006094263 A2 | 9/2006 |
| WO | 2007041664 A1 | 4/2007 |
| WO | 2008082889 A2 | 7/2008 |
| WO | 2009015385 A1 | 1/2009 |
| WO | 2009056651 A1 | 5/2009 |
| WO | 2009142352 | 11/2009 |
| WO | 2010090677 A1 | 8/2010 |
| WO | 2012048854 A2 | 4/2012 |
| WO | 2012134240 A2 | 10/2012 |

OTHER PUBLICATIONS

Glogau, et al., "Results of a Randomized, Double-Blind, Placebo-Controlled Study to Evaluate the Efficacy and Safety of a Botulinum Toxin Type A Topical Gel for the Treatment of Moderate-to-Severe Lateral Canthal Lines", Journal of Drugs in Dermatology, vol. 11, No. 1, Jan. 1, 2012, pp. 38-45.

Roy, et al., "Effect of pH on Stability of Recombinant Botulinum Serotype A Vaccine in Aqueous Solution and During Storage of Freeze-Dried Formulations", Journal of Pharmaceutical Sciences, vol. 97, No. 12, Dec. 1, 2008, pp. 5132-5146.

Waugh, et al., "Topical Neurotoxin, in Botulinum Toxin", Procedures in Cosmetic Dermatology, 3rd Edition, Chapter 10, Nov. 2012, pp. 67-71.

Brooks et al., "Tat peptide-mediated cellular delivery: back to basics," Advanced Drug Delivery Reviews, 57, 2005, pp. 559-577.

Calnan et al., "Analysis of arginine-rich peptides from the HIV Tat protein reveals unusual features of RNA-protein recognition", Genes & development, 5: 201-210, 1991.

Madison, Kathi C., "Barrier Function of the Skin: 'La Raison d'Etre' of the Epidermis", The Society for Investigative Dermatology, 2003, 121, 231-241.

Simpson, Lance, "Identification of the Major Steps in Botulinum Toxin Action", Annu. Rev. Pharmacol. Toxicol, 2004, 44:167-93.

Goodnough, Michael Charles, "A disertation entitled, Characterization and Stabilization of Clostridium Botulinum Neurotoxin for Medical Use", Thesis submitted in partial fulfillment of the requirements for the degree of Doctor of Philosophy (Food Science), at the University of Wisconsin-Madison, 1994, pp. 1-231.

* cited by examiner

Lateral to Midline Injection (A)  Midline injection (B)

SEQUENCE LISTING

```
<160> NUMBER OF SEQ ID NOS: 7

<210> SEQ ID NO 1
<211> LENGTH: 45
<212> TYPE: PRT
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: misc_feature
<222> LOCATION: (1)..(20)
<223> OTHER INFORMATION: This region may encompass 0-20 residues
<220> FEATURE:
<221> NAME/KEY: misc_feature
<222> LOCATION: (21)..(45)
<223> OTHER INFORMATION: This region may encompass any odd integer from
      5-25 residues

<400> SEQUENCE: 1

Gly Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg Arg
            20                  25                  30

Arg Arg Arg Arg Arg Arg Arg Arg Arg Arg Arg Arg Arg
        35                  40                  45

<210> SEQ ID NO 2
<211> LENGTH: 51
<212> TYPE: PRT
<213> ORGANISM: Human immunodeficiency virus
<220> FEATURE:
<221> NAME/KEY: misc_feature
<222> LOCATION: (1)..(20)
<223> OTHER INFORMATION: This region may encompass 0-20 residues
<220> FEATURE:
<221> NAME/KEY: misc_feature
<222> LOCATION: (32)..(51)
<223> OTHER INFORMATION: This region may encompass 0-20 residues

<400> SEQUENCE: 2

Gly Gly Gly Gly Gly Gly Gly Gly Gly Gly Gly Gly Gly Gly Gly Gly
1               5                   10                  15

Gly Gly Gly Gly Arg Gly Arg Asp Asp Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50

<210> SEQ ID NO 3
<211> LENGTH: 51
<212> TYPE: PRT
```

```
<213> ORGANISM: Human immunodeficiency virus
<220> FEATURE:
<221> NAME/KEY: misc_feature
<222> LOCATION: (1)..(20)
<223> OTHER INFORMATION: This region may encompass 0-20 residues
<220> FEATURE:
<221> NAME/KEY: misc_feature
<222> LOCATION: (32)..(51)
<223> OTHER INFORMATION: This region may encompass 0-20 residues

<400> SEQUENCE: 3

Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Gly
            20                  25                  30

Gly Gly Gly Gly Gly Gly Gly Gly Gly Gly Gly Gly Gly Gly Gly
            35                  40                  45

Gly Gly Gly
    50

<210> SEQ ID NO 4
<211> LENGTH: 49
<212> TYPE: PRT
<213> ORGANISM: Human immunodeficiency virus
<220> FEATURE:
<221> NAME/KEY: misc_feature
<222> LOCATION: (1)..(20)
<223> OTHER INFORMATION: This region may encompass 0-20 residues
<220> FEATURE:
<221> NAME/KEY: misc_feature
<222> LOCATION: (30)..(49)
<223> OTHER INFORMATION: This region may encompass 0-20 residues

<400> SEQUENCE: 4

Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Gly Gly Gly
            20                  25                  30

Gly Gly Gly Gly Gly Gly Gly Gly Gly Gly Gly Gly Gly Gly Gly
            35                  40                  45

Gly

<210> SEQ ID NO 5
<211> LENGTH: 19
<212> TYPE: PRT
<213> ORGANISM: Unknown
<220> FEATURE:
<223> OTHER INFORMATION: Description of Unknown: Antennapedia sequence

<400> SEQUENCE: 5

Ser Gly Arg Gln Ile Lys Ile Trp Phe Gln Asn Arg Arg Met Lys Trp
1               5                   10                  15

Lys Lys Cys

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Arg Arg Arg Arg Arg Arg
1               5                   10
```

```
<210> SEQ ID NO 7
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Arg Lys Lys Arg Arg Gln Arg Arg Arg Gly Lys Lys Lys Lys Lys
1               5                   10                  15

Lys Lys Lys Lys Lys Lys Lys Lys Gly Arg Lys Lys Arg Arg Gln
            20                  25                  30

Arg Arg Arg
        35
```

INJECTABLE BOTULINUM TOXIN FORMULATIONS

RELATED PATENT APPLICATION

This application is a divisional of U.S. Non-Provisional patent application Ser. No. 15/937,388 filed on Mar. 27, 2018, which is a divisional of U.S. Non-Provisional patent application Ser. No. 13/141,935 filed on Jul. 9, 2011, now U.S. Pat. No. 9,956,435 that issued on May 1, 2018, which is a 371 of International Patent Application No. PCT/US2009/069576 filed on Dec. 28, 2009, which claims the benefit of priority under 35 U.S.C. § 119 to U.S. Provisional Patent Application No. 61/142,063, filed Dec. 31, 2008, the contents of which are incorporated herein by reference in its entirety.

FIELD OF THE INVENTION

This invention relates to novel injectable compositions comprising botulinum toxin that may be administered to a subject for various therapeutic, aesthetic and/or cosmetic purposes.

BACKGROUND OF THE INVENTION

Skin protects the body's organs from external environmental threats and acts as a thermostat to maintain body temperature. It consists of several different layers, each with specialized functions. The major layers include the epidermis, the dermis and the hypodermis. The epidermis is a stratifying layer of epithelial cells that overlies the dermis, which consists of connective tissue. Both the epidermis and the dermis are further supported by the hypodermis, an internal layer of adipose tissue.

The epidermis, the topmost layer of skin, is only 0.1 to 1.5 millimeters thick (Inlander, Skin, New York, N.Y.: People's Medical Society, 1-7 (1998)). It consists of keratinocytes and is divided into several layers based on their state of differentiation. The epidermis can be further classified into the stratum corneum and the viable epidermis, which consists of the granular melphigian and basal cells. The stratum corneum is hygroscopic and requires at least 10% moisture by weight to maintain its flexibility and softness. The hygroscopicity is attributable in part to the water-holding capacity of keratin. When the horny layer loses its softness and flexibility it becomes rough and brittle, resulting in dry skin.

The dermis, which lies just beneath the epidermis, is 1.5 to 4 millimeters thick. It is the thickest of the three layers of the skin. Most of the skin's structures, including sweat and oil glands (which secrete substances through openings in the skin called pores, or comedos), hair follicles, nerve endings, and blood and lymph vessels are found in the dermis (Inlander, Skin, New York, N.Y.: People's Medical Society, 1-7 (1998)). However, the main components of the dermis are collagen and elastin.

The hypodermis is the deepest layer of the skin. It acts both as an insulator for body heat conservation and as a shock absorber for organ protection (Inlander, Skin, New York, N.Y.: People's Medical Society, 1-7 (1998)). In addition, the hypodermis also stores fat for energy reserves. The pH of skin is normally between 5 and 6. This acidity is due to the presence of amphoteric amino acids, lactic acid, and fatty acids from the secretions of the sebaceous glands. The term "acid mantle" refers to the presence of the water-soluble substances on most regions of the skin. The buffering capacity of the skin is due in part to these secretions stored in the skin's horny layer.

Wrinkles, one of the telltale signs of aging, can be caused by biochemical, histological, and physiologic changes that accumulate from environmental damage to the skin. (Benedetto, "International Journal of Dermatology," 38:641-655 (1999)). In addition, there are other secondary factors that can cause characteristic folds, furrows, and creases of facial wrinkles (Stegman et al., *The Skin of the Aging Face Cosmetic Dermatological Surgery*, $2^{nd}$ ed., St. Louis, Mo.: Mosby Year Book: 5-15 (1990)). These secondary factors include the constant pull of gravity, frequent and constant positional pressure on the skin (e.g., during sleep), and repeated facial movements caused by the contraction of facial muscles (Stegman et al., The Skin of the Aging Face Cosmetic Dermatological Surgery, $2^{nd}$ ed., St. Louis, Mo.: Mosby Year Book: 5-15 (1990)).

Different techniques have been utilized in order to potentially mollify some of the signs of aging. These techniques range from facial moisturizers containing alpha hydroxy acids and retinol to surgical procedures and injections of neurotoxins. For example, in 1986, Jean and Alastair Carruthers, a husband and wife team consisting of an ocuplastic surgeon and a dermatologist, developed a method of using the type A form of botulinum toxin for treatment of movement-associated wrinkles in the glabella area (Schantz and Scott, In Lewis G. E. (Ed) *Biomedical Aspects of Botulinum*, New York: Academic Press, 143-150 (1981)). The Carruthers' use of the type A form of botulinum toxin for the treatment of wrinkles led to the seminal publication of this approach in 1992 (Schantz and Scott, In Lewis G. E. (Ed) *Biomedical Aspects of Botulinum*, New York: Academic Press, 143-150 (1981)). By 1994, the same team reported experiences with other movement-associated wrinkles on the face (Scott, Ophthalmol, 87:1044-1049 (1980)). This in turn led to the birth of the era of cosmetic treatment using the type A form of botulinum toxin.

The type A form of botulinum toxin is reported to be the most lethal natural biological agent known to man. Spores of *C. botulinum* are found in soil and can grow in improperly sterilized and sealed food containers. Botulism, which may be fatal, may be caused by the ingestion of the bacteria. Botulinum toxin acts to produce paralysis of muscles by preventing synaptic transmission by inhibiting the release of acetylcholine across the neuromuscular junction, and is thought to act in other ways as well. Its action essentially blocks signals that normally would cause muscle spasms or contractions, resulting in paralysis. During the last decade, botulinum toxin's muscle paralyzing activity has been harnessed to achieve a variety of therapeutic effects. Controlled administration of botulinum toxin has been used to provide muscle paralysis to treat a variety of medical conditions, for example, neuromuscular disorders characterized by hyperactive skeletal muscles. Conditions that have been treated with botulinum toxin include hemifacial spasm, adult onset spasmodic torticollis, anal fissure, blepharospasm, cerebral palsy, cervical dystonia, migraine headaches, strabismus, temporomandibular joint disorder, and various types of muscle cramping and spasms. More recently, the muscle-paralyzing effects of botulinum toxin have been applied to therapeutic and cosmetic facial applications such as treatment of wrinkles, frown lines, and other results of spasms or contractions of facial muscles.

In addition to the type A form of botulinum toxin, there are seven other serologically distinct forms of botulinum toxin that are also produced by the gram-positive bacteria *Clostridium botulinum*. Of these eight serologically distinct types of botulinum toxin, the seven that can cause paralysis have been designated botulinum toxin serotypes A, B, C, D, E, F and G. Each of these is distinguished by neutralization with type-specific antibodies. The molecular weight of each of the botulinum toxin proteins is about 150 kD. Due to the molecule size and molecular structure of botulinum toxin, it cannot cross stratum corneum and the multiple layers of the underlying skin architecture. The different serotypes of botulinum toxin vary in the effect and in the severity and duration of the paralysis they evoke in different animal species. For example, in rats, it has been determined that botulinum toxin type A is 500 times more potent than botulinum toxin type B, as measured by the rate of paralysis. Additionally, botulinum toxin type B has been determined to be non-toxic in primates at a dose of 480 U/kg, about 12 times the primate $LD_{50}$ for type A.

As released by *Clostridium botulinum* bacteria, botulinum toxin is a component of a toxin complex containing the approximately 150 kD botulinum toxin protein molecule along with associated non-toxin proteins. These endogenous non-toxin proteins are believed to include a family of hemagglutinin proteins, as well as non-hemagglutinin protein. The non-toxin proteins have been reported to stabilize the botulinum toxin molecule in the toxin complex and protect it against denaturation by digestive acids when toxin complex is ingested. Thus, the non-toxin proteins of the toxin complex protect the activity of the botulinum toxin and thereby enhance systemic penetration when the toxin complex is administered via the gastrointestinal tract. Additionally, it is believed that some of the non-toxin proteins specifically stabilize the botulinum toxin molecule in blood.

The presence of non-toxin proteins in the toxin complexes typically causes the toxin complexes to have molecular weights that are greater than that of the bare botulinum toxin molecule, which is about 150 kD, as previously stated. For example, *Clostridium botulinum* bacteria can produce botulinum type A toxin complexes that have molecular weights of about 900 kD, 500 kD or 300 kD. Botulinum toxin types B and C are produced as complexes having a molecular weight of about 700 kD or about 500 kD. Botulinum toxin type D is produced as complexes having molecular weights of about 300 kD or 500 kD. Botulinum toxin types E and F are only produced as complexes having a molecular weight of about 300 kD.

To provide additional stability to botulinum toxin, the toxin complexes are conventionally stabilized by combining the complexes with albumin during manufacturing. For example, BOTOX® (Allergan, Inc., Irvine, Calif.) is a botulinum toxin-containing formulation that contains 100 U of type A botulinum toxin with accessory proteins, 0.5 milligrams of human albumin, and 0.9 milligrams of sodium chloride. The albumin serves to bind and to stabilize toxin complexes in disparate environments, including those associated with manufacturing, transportation, storage, and administration.

Typically, the botulinum toxin is administered to patients by carefully controlled injections of compositions containing botulinum toxin complex and albumin. However, there are several problems associated with this approach. Not only are the injections painful, but typically large subdermal wells of toxin are locally generated around the injection sites, in order to achieve the desired therapeutic or cosmetic effect. The botulinum toxin may migrate from these subdermal wells to cause unwanted paralysis in surrounding areas of the body. This problem is exacerbated when the area to be treated is large and many injections of toxin are required to treat the area. Moreover, because the injected toxin complexes contain non-toxin proteins and albumin that stabilize the botulinum toxin and increase the molecular weight of the toxin complex, the toxin complexes have a long half-life in the body and may cause an undesirable antigenic response in the patient. For example, some patients will, over time, develop an allergy to the albumin used as a stabilizer in current commercial formulations. Also, the toxin complexes may induce the immune system of the patient to form neutralizing antibodies, so that larger amounts of toxin are required in subsequent administrations to achieve the same effect. When this happens, subsequent injections must be carefully placed so that they do not release a large amount of toxin into the bloodstream of the patient, which could lead to fatal systemic poisoning, especially since the non-toxin proteins and albumin stabilize the botulinum toxin in blood.

In view of the drawbacks associated with current botulinum toxin formulations, it would be highly desirable to have an injectable botulinum toxin formulation that is efficacious and stable, but exhibits reduced antigenicity and a lower tendency to diffuse locally after injection. It would also be desirable to use such a botulinum toxin formulation for various therapeutic, aesthetic and/or cosmetic purposes.

SUMMARY OF THE INVENTION

This invention provides injectable compositions comprising botulinum toxin non-covalently associated with a positively charged carrier molecule. In preferred embodiments, the compositions of the invention possess one or more advantages over conventional commercial botulinum toxin formulations, such as BOTOX® or MYOBLOC®. For instance, in certain embodiments, the compositions may exhibit one or more advantages over conventional injectable botulinum formulations, including reduced antigenicity, a reduced tendency to undergo diffusion into surrounding tissue following injection, increased duration of clinical efficacy or enhanced potency relative to conventional botulinum toxin formulations, faster onset of clinical efficacy, and/or improved stability.

One aspect of this invention is the recognition that certain non-native molecules (i.e., molecules not found in botulinum toxin complexes obtained from *Clostridium botulinum* bacteria) can be added to botulinum toxin, botulinum toxin complexes, and in particular reduced botulinum toxin complexes (as defined herein), to improve toxin diffusion through tissues. The non-native molecules associate non-covalently with the toxin and act as penetration enhancers that improve the ability of the toxin to reach target structures after injection. Furthermore, the non-native molecules may increase the stability of the toxin prior to and after injection. By way of example, the penetration enhancers may be positively charged carriers, such as cationic peptides, which have no inherent botulinum-toxin-like activity and which also contain one or more protein transduction domains as described herein.

Another embodiment of this invention is to provide a composition comprising botulinum toxin, a botulinum toxin complex (or a reduced protein botulinum toxin complex including just the 150 kD neurotoxin itself or the neurotoxin with some, but not all, of the native complex proteins) and a positively charged carrier.

The invention further relates to a method for producing a biologic effect by injecting an effective amount of the compositions of this invention to a subject or patient in need of such treatment. The biologic effect may include, for example, muscle paralysis, reduction of hypersecretion or sweating, treatment of neurologic pain or migraine headache, management of rhinitis or sinusitis, treatment of hyperactive bladder, reduction of muscle spasms, prevention or reduction of acne, reduction or enhancement of an immune response, reduction of wrinkles, or prevention or treatment of various other disorders.

This invention also provides kits for preparing formulations containing a botulinum toxin, a botulinum toxin complex, or a reduced protein botulinum toxin complex and positively charged carrier, or a premix that may in turn be used to produce such a formulation. Also provided are kits that contain means for sequentially administering a botulinum toxin complex (or a reduced botulinum toxin complex including just the 150 KD neurotoxin itself or the neurotoxin with some native complex proteins) and a positively charged carrier.

BRIEF DESCRIPTION OF THE FIGURES

FIG. 2A shows the hind leg of a mouse injected with a dark dye to indicate the portion of a mouse's gastrocnemius muscle that is affected by lateral-to-midline injection. FIG. 2B shows the hind leg of a mouse injected with a dark dye to indicate the portion of a mouse's gastrocnemius muscle that is affected by midline injection.

DETAILED DESCRIPTION OF THE INVENTION

Figure 1:
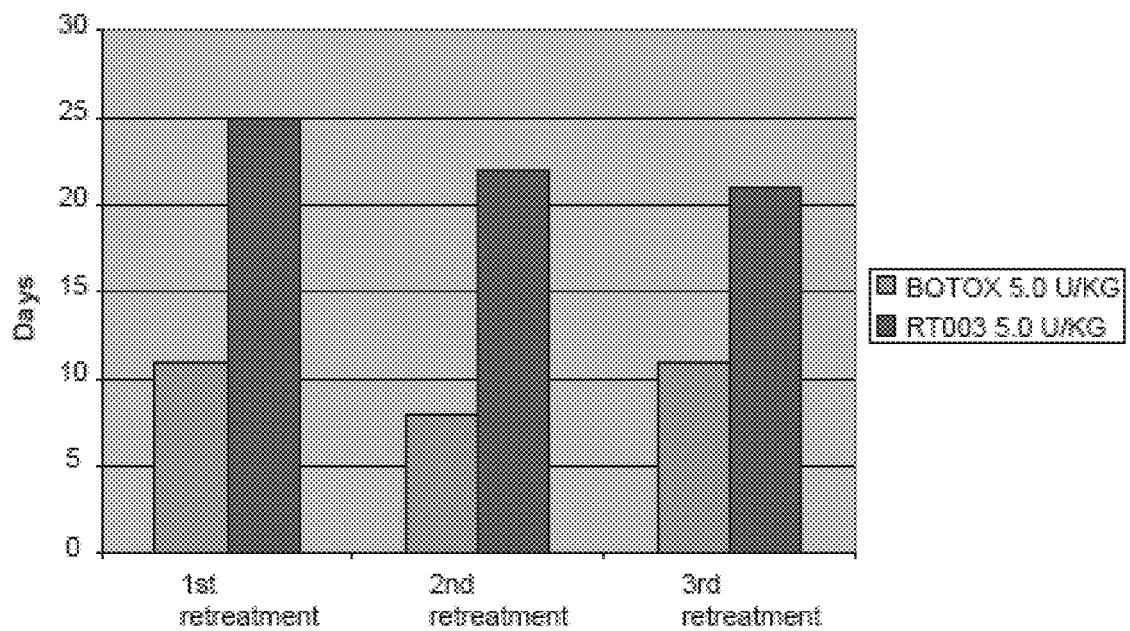
FIG. 1: A bar graph showing the required time to return to the baseline DAS value (0.4) following repeated administration of either RT003 or BOTOX®

This invention relates to novel injectable compositions comprising botulinum toxin, a botulinum toxin complex, or a reduced botulinum toxin complex. In preferred embodiments, the compositions stabilize the toxin or enable the transport or delivery of toxin through tissues after injection such that the toxin has reduced antigenicity, a better safety profile, enhanced potency, faster onset of clinical efficacy and/or longer duration of clinical efficacy compared to conventional commercial botulinum toxin complexes that are bound to exogenous albumin (e.g., BOTOX® or MYOBLOC®). The compositions of the invention may be used as injectable applications for providing a botulinum toxin to a subject, for various therapeutic, aesthetic and/or cosmetic purposes, as described herein. The compositions of the invention also have an improved safety profile over other compositions and methods of delivery of botulinum toxin. In addition, these compositions can afford beneficial reductions in immune responses to the botulinum toxin.

The term "botulinum toxin" as used herein may refer to any of the known types of botulinum toxin (e.g., 150 kD botulinum toxin protein molecules associated with the different serotypes of *C. botulinum*), whether produced by the bacterium or by recombinant techniques, as well as any such types that may be subsequently discovered including newly discovered serotypes, and engineered variants or fusion proteins. As mentioned above, currently seven immunologically distinct botulinum neurotoxins have been characterized, namely botulinum neurotoxin serotypes A, B, C, D, E, F and G, each of which is distinguished by neutralization with type-specific antibodies. The botulinum toxin serotypes are commercially available, for example, from Sigma-Aldrich (St. Louis, Mo.) and from Metabiologics, Inc. (Madison, Wis.), as well as from other sources. The different serotypes of botulinum toxin vary in the animal species that they affect and in the severity and duration of the paralysis they evoke. At least two types of botulinum toxin, types A and B, are available commercially in formulations for treatment of certain conditions. Type A, for example, is contained in preparations of Allergan having the trademark BOTOX®$^M$ and of Ipsen having the trademark DYSPORT®, and type B is contained in preparations of Elan having the trademark MYOBLOC®.

The term "botulinum toxin" used in the compositions of this invention can alternatively refer to a botulinum toxin derivative, that is, a compound that has botulinum toxin activity but contains one or more chemical or functional alterations on any part or on any amino acid chain relative to naturally occurring or recombinant native botulinum toxins. For instance, the botulinum toxin may be a modified neurotoxin that is a neurotoxin which has at least one of its amino acids deleted, modified or replaced, as compared to a native form, or the modified neurotoxin can be a recombinantly produced neurotoxin or a derivative or fragment thereof. For instance, the botulinum toxin may be one that has been modified in a way that, for instance, enhances its properties or decreases undesirable side effects, but that still retains the desired botulinum toxin activity. Alternatively the botulinum toxin used in this invention may be a toxin prepared using recombinant or synthetic chemical techniques, e.g. a recombinant peptide, a fusion protein, or a hybrid neurotoxin, for example prepared from subunits or domains of different botulinum toxin serotypes (see U.S. Pat. No. 6,444,209, for instance). The botulinum toxin may also be a portion of the overall molecule that has been shown to possess the necessary botulinum toxin activity, and in such case may be used per se or as part of a combination or conjugate molecule, for instance a fusion protein. Alternatively, the botulinum toxin may be in the form of a botulinum toxin precursor, which may itself be non-toxic, for instance a non-toxic zinc protease that becomes toxic on proteolytic cleavage.

The term "botulinum toxin complex" or "toxin complex" as used herein refers to the approximately 150 kD botulinum toxin protein molecule (belonging to any one of botulinum toxin serotypes A-G), along with associated endogenous non-toxin proteins (i.e., hemagglutinin protein and non-toxin non-hemagglutinin protein produced by *Clostridium botulinum* bacteria). Note, however, that the botulinum toxin complex need not be derived from *Clostridium botulinum* bacteria as one unitary toxin complex. For example, botulinum toxin or modified botulinum toxin may be recombinantly prepared first and then subsequently combined with the non-toxin proteins. Recombinant botulinum toxin can also be purchased (e.g., from List Biological Laboratories, Campbell, Calif.) and then combined with non-toxin proteins.

This invention also contemplates modulation of the stability of botulinum toxin molecules through the addition of one or more exogenous stabilizers, the removal of endogenous stabilizers, or a combination thereof. For example, this invention contemplates the use of "reduced botulinum toxin complexes", in which the botulinum toxin complexes have reduced amounts of non-toxin protein compared to the amounts naturally found in botulinum toxin complexes produced by *Clostridium botulinum* bacteria. In one embodiment, reduced botulinum toxin complexes are prepared using any conventional protein separation method to extract a fraction of the hemagglutinin protein or non-toxin non-hemagglutinin protein from botulinum toxin complexes derived from *Clostridium botulinum* bacteria. For example, reduced botulinum toxin complexes may be produced by dissociating botulinum toxin complexes through exposure to red blood cells at a pH of 7.3 (e.g., see EP 1514556 A1, hereby incorporated by reference). HPLC, dialysis, columns, centrifugation, and other methods for extracting proteins from proteins can be used. Alternatively, when the reduced botulinum toxin complexes are to be produced by combining synthetically produced botulinum toxin with non-toxin proteins, one may simply add less hemagglutinin or non-toxin, non-hemagglutinin protein to the mixture than what would be present for naturally occurring botulinum toxin complexes. Any of the non-toxin proteins (e.g., hemagglutinin protein or non-toxin non-hemagglutinin protein or both) in the reduced botulinum toxin complexes according to the invention may be reduced independently by any amount. In certain exemplary embodiments, one or more non-toxin proteins are reduced by at least about 0.5%, 1%, 3%, 5%, 10%, 20%, 30%, 40%, 50%, 60%, 70%, 80%, 90% or 100% compared to the amounts normally found in botulinum toxin complexes. As noted above, *Clostridium botulinum* bacteria produce seven different serotypes of toxin and commercial preparations are manufactured with different relative amounts of non-toxin proteins (i.e. different amount of toxin complexes). For example, MYOBLOC™ has 5000 U of Botulinum toxin type B per ml with 0.05% human serum albumin, 0.01 M sodium succinate, and 0.1 M sodium chloride. DYSPORT™ has 500 U of botulinum toxin type A-hemagglutinin complex with 125 mcg albumin and 2.4 mg lactose. In certain embodiments, substantially all of the non-toxin protein (e.g., greater than 95%, 96%, 97%, 98% or 99% of the hemagglutinin protein and non-toxin non-hemagglutinin protein) that would normally be found in botulinum toxin complexes derived from *Clostridium botulinum* bacteria is removed from the botulinum toxin complex. Furthermore, although the amount endogenous non-toxin proteins may be reduced by the same amount in some cases, this invention also contemplates reducing each of the endogenous non-toxin proteins by different amounts, as well as reducing at least one of the endogenous non-toxin proteins, but not the others.

As noted above, an exogenous stabilizer (e.g., albumin) is typically added to stabilize botulinum toxin formulations. For instance, in the case of BOTOX®, 0.5 mg of human albumin per 100 U of type A botulinum toxin complex to stabilize the complex. Generally, the amount of exogenous stabilizer that may be added to stabilize the compositions according to the invention is not particularly limited. In some embodiments, the amount of added stabilizer may be less than the amount conventionally added, owing to the ability of positively charged carriers of the invention to act as a stabilizer in its own right. For instance, the amount of added exogenous albumin can be any amount less than the conventional thousand-fold excess of exogenous albumin and, in certain exemplary embodiments of the invention, is only about 0.25, 0.20, 0.15, 0.10, 0.01, 0.005, 0.001, 0.0005, 0.00001, 0.000005, 0.000001, or 0.0000001 mg per 100 U of botulinum toxin. In one embodiment, no exogenous albumin is added as a stabilizer to the compositions of the invention.

According to the present invention, a positively charged carrier molecule having protein transduction domains or efficiency groups, as described herein, has been found suitable as a transport system for a botulinum toxin, enabling toxin to be injected with improved penetration to target structures such as muscles and/or other skin-associated structures. The transport occurs without covalent modification of the botulinum toxin. Besides enhancing penetration of botulinum toxin, the positively charged carriers of the invention may, in certain preferred embodiments, stabilize the botulinum toxin against degradation. In such embodiments, the hemagglutinin protein and non-toxin, non-hemagglutinin protein that are normally present to stabilize the botulinum toxin may be reduced or omitted entirely. Similarly, the exogenous albumin that is normally added during manufacturing may be omitted.

By the use of the terms "positively charged" or "cationic" in connection with the term "carrier", it is meant that the carrier has a positive charge under at least some solution-phase conditions, more preferably under at least some physiologically compatible conditions. More specifically, "positively charged" and "cationic" as used herein, means that the group in question contains functionalities that are charged under all pH conditions, for instance, a quaternary amine, or contains a functionality which can acquire positive charge under certain solution-phase conditions, such as pH changes in the case of primary amines. More preferably, "positively charged" or "cationic" as used herein refers to those groups that have the behavior of associating with anions over physiologically compatible conditions. Polymers with a multiplicity of positively-charged moieties need not be homopolymers, as will be apparent to one skilled in the art. Other examples of positively charged moieties are well known in the prior art and can be employed readily, as will be apparent to those skilled in the art.

Generally, the positively-charged carrier (also referred to as a "positively charged backbone") is typically a chain of atoms, either with groups in the chain carrying a positive charge at physiological pH, or with groups carrying a positive charge attached to side chains extending from the backbone. In certain preferred embodiments, the positively charged backbone is a cationic peptide. As used herein, the term "peptide" refers to an amino acid sequence, but carries no connotation with respect to the number of amino acid residues within the amino acid sequence. Accordingly, the term "peptide" may also encompass polypeptides and proteins. In certain preferred embodiments, the positively charged backbone itself will not have a defined enzymatic or therapeutic biologic activity. In certain embodiments, the backbone is a linear hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) but can be a heteropolymer. In one group of embodiments, the positively charged backbone is a polypropyleneamine wherein a number of the amine nitrogen atoms are present as ammonium groups (tetra-substituted) carrying a positive charge. In another embodiment, the positively charged backbone is a nonpeptidyl polymer, which may be a hetero- or homo-polymer such as a polyalkyleneimine, for example a polyethyleneimine or polypropyleneimine, having a molecular weight of from about 10,000 to about 2,500,000, preferably from about 100,000 to about 1,800,000, and most preferably from about 500,000 to about 1,400,000. In another group of embodiments, the backbone has attached a plurality of side-chain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups. The association between the positively charged carrier and the botulinum toxin, reduced bo is by non-covalent interaction, non-limiting examples of which include ionic interactions, hydrogen bonding, van der Waals forces, or combinations thereof.

In one group of embodiments, the positively charged backbone is a polypeptide having multiple positively charged sidechain groups (e.g., lysine, arginine, ornithine, homoarginine, and the like). Preferably, the polypeptide has a molecular weight from about 100 to about 1,500,000, more preferably from about 500 to about 1,200,000, most preferably from about 1000 to about 1,000,000. One of skill in the art will appreciate that when amino acids are used in this portion of the invention, the sidechains can have either the D- or L-form (R or S configuration) at the center of attachment. In certain preferred embodiments, the polypeptide has a molecular weight from about 500 to about 5000, more preferably from 1000 to about 4000, more preferably from 2000 to about 3000.

Alternatively, the backbone may comprise amino acid analogs and/or synthetic amino acids. The backbone may also be an analog of a polypeptide such as a peptoid. See, for example, Kessler, Angew. Chem. Int. Ed. Engl. 32:543 (1993); Zuckermann et al. Chemtracts-Macromol. Chem. 4:80 (1992); and Simon et al. Proc. Nat'l. Acad. Sci. USA 89:9367 (1992)). Briefly, a peptoid is a polyglycine in which the sidechain is attached to the backbone nitrogen atoms rather than the α-carbon atoms. As above, a portion of the sidechains will typically terminate in a positively charged group to provide a positively charged backbone component. Synthesis of peptoids is described in, for example, U.S. Pat. No. 5,877,278, which is hereby incorporated by reference in its entirety. As the term is used herein, positively charged backbones that have a peptoid backbone construction are considered "non-peptide" as they are not composed of amino acids having naturally occurring sidechains at the alpha-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene (—NHCH$_2$—) or the reversed methyleneamino (—CH$_2$NH—) groups, keto-methylene (—COCH$_2$—) groups, phosphinate (—PO$_2$RCH$_2$—), phosphonamidate and phosphonamidate ester (—PO$_2$RNH—), reverse peptide (—NHCO—), trans-alkene (—CR=CH—), fluoroalkene (—CF=CH—), dimethylene (—CH$_2$CH$_2$—), thioether (—CH$_2$S—), hydroxyethylene (—CH(OH)CH$_2$—), methyleneoxy (—CH$_2$O—), tetrazole (CN$_4$), sulfonamido (—SO$_2$NH—), methylenesulfonamido (—CHRSO$_2$NH—), reversed sulfonamide (—NHSO$_2$—), and backbones with malonate and/or gem-diamino-alkyl subunits, for example, as reviewed by Fletcher et al. ((1998) Chem. Rev. 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group. For example, the sulfonamide-linked backbones (—SO$_2$NH— and —NHSO$_2$—) can have sidechain groups attached to the nitrogen atoms. Similarly, the hydroxyethylene (—CH(OH)CH$_2$—) linkage can bear a sidechain group attached to the hydroxy substituent. One of skill in the art can readily adapt the other linkage chemistries to provide positively charged sidechain groups using standard synthetic methods.

In one embodiment, the positively charged backbone is a polypeptide having protein transduction domains (also referred to as efficiency groups). As used herein, an efficiency group or protein transduction domain is any agent that has the effect of promoting the translocation of the positively charged backbone through a tissue or cell membrane. Non-limiting examples of protein transduction domains or efficiency groups include -(gly)$_{n1}$-(arg)$_{n2}$, HIV-TAT or fragments thereof, or the protein transduction domain of Antennapedia, or a fragment thereof, in which the subscript n1 is an integer of from 0 to 20, more preferably 0 to 8, still more preferably 2 to 5, and the subscript n2 is independently an odd integer of from about 5 to about 25, more preferably about 7 to about 17, most preferably about 7 to about 13. In some embodiments, the HIV-TAT fragment does not contain the cysteine-rich region of the HIV-TAT molecule, in order to minimize the problems associated with disulfide aggregation. Still further preferred are those embodiments in which the HIV-TAT fragment has the formula (gly)$_p$-RGRDDRRQRRR-(gly)$_q$, (gly)$_p$-YGRKKRRQRRR-(gly)$_q$ or (gly)$_p$-RKKRRQRRR-(gly)$_q$ wherein the subscripts p and q are each independently an integer of from 0 to 20 and the fragment is attached to the backbone via either the C-terminus or the N-terminus of the fragment. In certain preferred embodiments, p is one and q is zero or p is zero and q is one. Preferred HIV-TAT fragments are those in which the subscripts p and q are each independently integers of from 0 to 8, more preferably 0 to 5. In another preferred embodiment the positively charged side chain or branching group is the Antennapedia (Antp) protein transduction domain (PTD), or a fragment thereof that retains activity. These are known in the art, for instance, from Console et al., *J. Biol. Chem.* 278:35109 (2003) and a non-limiting example of a Antp PTD contemplated by this invention is SGRQIKIWFQNRRMKWKKC.

Preferably the positively charged carrier includes sidechain positively charged protein transduction domains in an amount of at least about 0.01%, as a percentage of the total carrier weight, preferably from about 0.01 to about 50 weight percent, more preferably from about 0.05 to about 45 weight percent, and most preferably from about 0.1 to about 30 weight %. For positively charged protein transduction domains having the formula -(gly)$_{n1}$-(arg)$_{n2}$, a preferred range is from about 0.1 to about 25%.

In another embodiment, the backbone portion is a polylysine and positively charged protein transduction domains are attached to the lysine sidechain amino groups or to the C- or N termini. In some preferred embodiments, the polylysine may have a molecular weight that is at least 100, 200, 300, 400, 500, 600, 700, 800, 900, 1000, 1500, 2000, 2500, 3000, 3500, 4000, 4500, 5000, 5500, or 6000 D, and less than about 2,000,000, 1,000,000, 500,000, 250,000, 100,000, 75,000, 50,000, and 25,000 D. Within the range of 100 to 2,000,000 D, it is contemplated that the lower and/or upper range may be increased or decreased, respectively, by 100, with each resulting sub-range being a specifically contemplated embodiment of the invention. In some exemplary embodiments, the polylysine has a molecular weight from about 1,000 to about 1,500,000 D, from about 2,000 to about 800,000 D, or from about 3,000 to about 200,000 D. In other exemplary embodiments, the polylysine has molecular weight from about 100 to about 10,000 D, from about 500 to about 5,000 D, from about 1,000 to about 4,000 D, from about 1,500 to about 3,500 D or from about 2,000 to about 3,000 D. In some embodiments, the polylysine contemplated by this invention can be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000. The selection of an appropriate polylysine will depend on the remaining components of the composition and will be sufficient to provide an overall net positive charge to the composition and provide a length that is preferably from one to four times the combined length of the negatively charged components. Preferred positively charged protein transduction domains or efficiency groups include, for example, -gly-gly-gly-arg-arg-arg-arg-arg-arg-arg ($-Gly_3Arg_7$) or HIV-TAT.

In another preferred embodiment the positively charged backbone is a polyalkyleneimine, non-limiting examples of which include polyethyleneimine, polypropyleneimine, and polybutyleneimine. In certain embodiments, the polyalkyleneimine has a molecular weight of at least 100, 200, 300, 400, 500, 600, 700, 800, 900, 1000, 1500, 2000, 2500, 3000, 3500, 4000, 4500, 5000, 5500, or 6000 D, and less than about 2,000,000, 1,000,000, 500,000, 250,000, 100,000, 75,000, 50,000, and 25,000 D. Within the range of 100 to 2,000,000 D, it is contemplated that the lower and/or upper range may be increased or decreased, respectively, by 100, with each resulting sub-range being a specifically contemplated embodiment of the invention.

In other embodiments of this invention, the carrier is a relatively short polylysine or polyethyleneimine (PEI) backbone (which may be linear or branched) and which has positively charged branching groups. Without wishing to be constrained by theory, it is believed that such carriers are useful for minimizing uncontrolled aggregation of the backbones and botulinum toxin in a therapeutic composition, which causes the transport efficiency to decrease dramatically. When the carrier is a relatively short linear polylysine or PEI backbone, the backbone will have a molecular weight of less than 75,000 D, more preferably less than 30,000 D, and most preferably, less than 25,000 D. When the carrier is a relatively short branched polylysine or PEI backbone, however, the backbone will have a molecular weight less than 60,000 D, more preferably less than 55,000 D, and most preferably less than 50,000 D.

In one particularly interesting embodiment, the non-native molecules are cationic peptides that have no inherent botulinum-toxin-like activity and that also contain one or more protein transduction domains as described herein. Without wishing to be bound by any particular scientific theory, it is believed that the peptides enhance tissue penetration of molecules associated in complex after injection, while enhancing stabilization of the botulinum toxin in skin and in vitro. It is believed that the enhanced tissue penetration afforded by these peptides in particular affords reduced antigenicity, a better safety profile, enhanced potency, faster onset of clinical efficacy or longer duration of clinical efficacy compared to conventional commercial botulinum toxin complexes that are bound to exogenous albumin (e.g., BOTOX® or MYOBLOC®).

In preferred embodiments, the concentration of positively charged carriers in the compositions according to the invention is sufficient to enhance the delivery of the botulinum toxin to molecular targets such as, for example, motor nerve plates. Furthermore, without wishing to be bound by theory, it is believed that the penetration rate follows receptor-mediated kinetics, such that tissue penetration increases with increasing amounts of penetration-enhancing-molecules up to a saturation point, upon which the transport rate becomes constant. Thus, in a preferred embodiment, the amount of added penetration-enhancing-molecules is equal to the amount that maximizes penetration rate right before saturation. A useful concentration range for the positively charged carrier in the injectable compositions of this invention is about 0.1 pg to about 1.0 mg per unit of the botulinum toxin composition as described herein. More preferably, the positively charged carrier in the compositions of the invention is present in the range of about 1.0 pg to 0.5 mg per unit of botulinum toxin.

Compositions of this invention are preferably in a form that permits injection into the skin or epithelium of subjects or patients, (i.e., humans or other mammals in need of the particular treatment). The term "in need" is meant to include both pharmaceutical or health-related needs (e.g., treating conditions involving undesirable facial muscle spasms), as well as cosmetic and subjective needs (e.g., altering or improving the appearance of facial tissue). In preferred embodiments, the compositions are prepared by mixing the botulinum toxin (either containing the associated non-toxin proteins or reduced associated non-toxin proteins) with the positively charged carrier, and usually with one or more additional pharmaceutically acceptable carriers or excipients. In their simplest form, they may contain an aqueous pharmaceutically acceptable diluent, such as buffered saline (e.g., phosphate buffered saline). However, the compositions may contain other ingredients typically found in injectable pharmaceutical or cosmeceutical compositions, including a dermatologically or pharmaceutically acceptable carrier, vehicle or medium that is compatible with the tissues to which it will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. As appropriate, compositions of the invention may comprise any ingredient conventionally used in the fields under consideration, and particularly in cosmetics and dermatology.

In terms of their form, compositions of this invention may include solutions, emulsions (including microemulsions), suspensions, gels, powders, or other typical solid or liquid compositions used for injection to muscle and other tissues where the compositions may be used. In preferred embodiments, the compositions of the invention are present in low-viscosity, sterile formulations suitable for injection with a syringe. The compositions of the invention may be in the form of a lyophilized powder that is reconstituted using a pharmaceutically acceptable liquid diluent prior to injection. In certain embodiments, the lyophilized powder is reconstituted with a liquid diluent to form an injectable formulation with a viscosity of about 0.1 to about 2000 cP, more preferably about 0.2 to about 500 cP, even more preferably about 0.3 to about 50 cP, and even more preferably about 0.4 to about 2.0 cP. The compositions of the invention may contain, in addition to the botulinum toxin and positively charged carrier, other ingredients typically used in such products, such as antimicrobials, hydration agents, tissue bulking agents or tissue fillers, preservatives, emulsifiers, natural or synthetic oils, solvents, surfactants, detergents, gelling agents, antioxidants, fillers, thickeners, powders, viscosity-controlling agents and water, and optionally including anesthetics, anti-itch actives, botanical extracts, conditioning agents, minerals, polyphenols, silicones or derivatives thereof, vitamins, and phytomedicinals.

The injectable compositions according to this invention may be in the form of controlled-release or sustained-release compositions which comprise botulinum toxin and positively charged carrier encapsulated or otherwise contained within a material such that they are released within the tissue in a controlled manner over time. The composition comprising the botulinum toxin and positively charged carrier may be contained within matrixes, liposomes, vesicles, microcapsules, microspheres and the like, or within a solid particulate material, all of which is selected and/or constructed to provide release of the botulinum toxin over time. The botulinum toxin and the positively charged carrier may be encapsulated together (i.e., in the same capsule) or separately (i.e., in separate capsules).

Botulinum toxin formulations according to the invention can be delivered by injection (typically using a syringe) to muscles underlying the skin, or to glandular structures within the skin, in an effective amount to produce paralysis, produce relaxation, alleviate contractions, prevent or alleviate spasms, reduce glandular output, or other desired effects. Local delivery of the botulinum toxin in this manner could afford dosage reductions, reduce toxicity and allow more precise dosage optimization for desired effects relative to injectable or implantable materials.

The compositions of the invention are administered to deliver an effective amount of the botulinum toxin. The term "effective amount" as used herein means an amount of a botulinum toxin as defined above that is sufficient to produce the desired muscular paralysis or other biological or aesthetic effect, but that implicitly is a safe amount, i.e. one that is low enough to avoid serious side effects. Desired effects include the relaxation of certain muscles with the aim of, for instance, decreasing the appearance of fine lines and/or wrinkles, especially in the face, or adjusting facial appearance in other ways such as widening the eyes, lifting the corners of the mouth, or smoothing lines that fan out from the upper lip, or the general relief of muscular tension. The last-mentioned effect, general relief of muscular tension, can be effected in the face or elsewhere. The compositions of the invention may contain an appropriate effective amount of the botulinum toxin for application as a single-dose treatment, or may be more concentrated, either for dilution at the place of administration or for use in multiple applications. Through the use of the positively charged carrier this invention, a botulinum toxin can be administered by injection to a subject for treating conditions such as wrinkles, undesirable facial muscle or other muscular spasms, hyperhidrosis, acne, or conditions elsewhere in the body in which relief of muscular ache or spasms is desired. The botulinum toxin is administered by injection to muscles or to other skin-associated or other target tissue structures. The administration may be made, for example, to the legs, shoulders, back (including lower back), axilla, palms, feet, neck, face, groin, dorsa of the hands or feet, elbows, upper arms, knees, upper legs, buttocks, torso, pelvis, or any other parts of the body where administration of the botulinum toxin is desired.

Administration of the injectable botulinum toxin-containing compositions of this invention may also be carried out to treat other conditions, including any condition for which prevention of synaptic transmission of or release of acetylcholine would confer a therapeutic benefit. For example, the conditions that may be treated by the compositions according to the invention include, without limitation, neurologic pain, migraine headache or other headache pain, overactive bladder, rhinitis, sinusitis, acne, dystonia, dystonic contractions (whether subjective or clinical), hyperhidrosis (whether subjective or clinical), and hypersecretion of one or more glands controlled by the cholinergic nervous system. The compositions of this invention may also be used for reducing or enhancing immune response, or treatment of other conditions for which administration of botulinum toxin by injection has been suggested or performed.

Most preferably, the compositions are administered by or under the direction of a physician or other health care professional. They may be administered in a single treatment or in a series of treatments over time. In preferred embodiments, a composition according to the invention is injected at a location or locations where an effect associated with botulinum toxin is desired. Because of its nature, the botulinum toxin preferably is administered at an amount, application rate, and frequency that will produce the desired result without producing any adverse or undesired results. For instance, in certain embodiments, the compositions of the invention are applied at a rate of from about 1 U to about 20,000 U, and more preferably from about 1 U to about 10,000 U botulinum toxin per $cm^2$ of skin surface. Higher dosages within these ranges may be employed, for example, in situations where the botulinum toxin is administered in conjunction with controlled release materials, as described herein. In certain embodiments, the botulinum toxin formulations of the invention are administered to provide 1 to 400 U, more preferably 10 to 350 U, even more preferably 30 to 250 U and most preferably 50 to 200 U of botulinum toxin per injection.

This invention also contemplates the use of a variety of delivery devices for injecting botulinum toxin-containing compositions described herein across skin. Such devices may include, without limitation, a needle and syringe, or may involve more sophisticated devices capable of dispensing and monitoring the dispensing of the composition, and optionally monitoring the condition of the subject in one or more aspects (e.g., monitoring the reaction of the subject to the substances being dispensed).

In some embodiments, the compositions can be pre-formulated and/or pre-installed in a delivery device as such. This invention also contemplates embodiments wherein the compositions are provided in a kit that stores one or more components separately from the remaining components. For example, in certain embodiments, the invention provides for a kit that separately stores botulinum toxin and the positively charged carrier for combining at or prior to the time of application. The amount of positively charged carrier or the concentration ratio of these molecules to the botulinum toxin will depend on which carrier is chosen for use in the composition in question. The appropriate amount or ratio of carrier molecule in a given case can readily be determined, for example, by conducting one or more experiments such as those described below.

In general, the invention also contemplates a method for administering botulinum toxin (alternatively as botulinum toxin complexes or reduced botulinum toxin complexes) to a subject or patient in need thereof, in which an effective amount of botulinum toxin is administered in conjunction with a positively charged carrier, as described herein. By "in conjunction with" it is meant that the two components (botulinum toxin and positively charged carrier) are administered in a combination procedure, which may involve either combining them prior to administration to a subject, or separately administering them, but in a manner such that they act together to provide the requisite delivery of an effective amount of the therapeutic protein. For example, a composition containing the positively charged carrier may first be administered to the skin of the subject, followed by application of a syringe or other device containing the botulinum toxin. The botulinum toxin may be stored in dry form in a syringe or other dispensing device and the positively charged carrier may be injected before application of the toxin so that the two act together, resulting in the desired tissue penetration enhancement. In that sense, thus, the two substances (positively charged carrier and botulinum toxin) act in combination or perhaps interact to form a composition or combination in situ. Accordingly, the invention also includes a kit with a device for dispensing botulinum toxin and a liquid, gel, or the like that contains the positively charged carrier, and that is suitable for injection to the skin or target tissue of a subject. Kits for administering the compositions of the inventions, either under direction of a health care professional or by the patient or subject, may also include a custom applicator suitable for that purpose.

The compositions of this invention are suitable for use in physiologic environments with pH ranging from about 4.5 to about 6.3, and may thus have such a pH. The compositions according to this invention may be stored either at room temperature or under refrigerated conditions.

It is understood that the following examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Duration of Local Muscle Paralysis in a Murine Model.

This example compares the duration of local muscle paralysis in mice injected with either RT003 or BOTOX®. RT003 is an exemplary injectable formulation according to the invention that contains type A botulinum toxin (purified to remove all endogenous non-toxin proteins) and positively charged carrier with the sequence RKKRRQRRRG-(K)$_{15}$-GRKKRRQRRR. BOTOX® also contains type A botulinum toxin, but exogenous albumin is added to stabilize the type A botulinum toxin molecule.

The muscle paralysis was measured using digit abduction score (DAS) assay as reported by Aoki, K. R. in "A comparison of the safety margins of botulinum neurotoxin serotypes A, B, and F in mice", *Toxicon* 2001; 39(12):1815-1820. In the DAS assay, a mouse is briefly suspended by its tail to cause a characteristic startle response in which the mouse extends its hind limbs and abducts its hind digits. The extent to which the mouse is able to exhibit this startle response is scored on a five-point scale (from 0-4), with zero representing a normal startle response and four representing maximal reduction in digit abduction and leg extension. The scoring is done by an observer with no knowledge of the extent to which the subject mouse has been treated with neurotoxin. The baseline score using the DAS assay was determined to be 0.4 for an untreated population of animals.

The study reported in this example involved ten animals (5 mice in RT003 group and 5 mice in BOTOX® group). Each of the animals was injected three times with the respective botulinum toxin formulation (i.e., RT003 or BOTOX®), with a 40-day period in between each dosing. After injection, the number of days that all of the animals in each test group was above the 0.4 baseline of the DAS assay was counted. The results, shown in FIG. 1, indicate that the DAS assay score for the RT003-treated group stayed above the 0.4 baseline value for 25, 22, and 21 days, following the first, second, and third treatment, respectively. In contrast, the DAS assay score for the BOTOX®-treated group stayed above the 0.4 baseline value for 11, 8, and 11 days, following the first, second, and third treatment, respectively.

These DAS assay data indicate that local muscle paralysis caused by the RT003 formulation lasts approximately twice as long as the local muscle paralysis caused by BOTOX®. This result has important implications for therapeutic uses of RT003 and other injectable botulinum toxin-containing compounds according to the invention. In particular, by using injectable compositions according to the invention, one can significantly reduce the frequency of follow-up injections required to maintain a particular cosmetic or therapeutic effect caused by the botulinum toxin. In turn, the reduced frequency of application can result in better long-term efficacy, as the subject is less prone to develop antibodies to the botulinum toxin.

Example 2

Injectable Botulinum Toxin Formulations with an Improved Safety Profile

Over the last few decades, botulinum toxin has found use as a therapeutic agent for treating a variety of conditions, including wrinkles, hyperhidrosis, and muscle spasms. However, as botulinum toxin is the most potent naturally occurring toxin known to humans, improper administration of the toxin can be extremely dangerous. For instance, accidental systemic delivery of botulinum toxin can lead to paralysis, difficulty breathing, and even death. Moreover, even if botulinum toxin were properly delivered to a localized region of the body as a part of a therapeutic treatment, the toxin has a natural tendency to diffuse over time, thereby increasing the risk of unwanted paralysis in other parts of the body. For example, when botulinum toxin is injected around the eyes to treat wrinkles, it may diffuse to the muscles that control the movement of the eyelids. If this happens, the eyelid muscles may become partially paralyzed, leading to a well known condition know as "eyelid droop," in which the eyelid is partially closed and interferes with normal vision.

One aspect of this invention is to provide injectable botulinum toxin formulations with an improved safety profile compared to currently available commercial botulinum toxin formulations. In preferred embodiments, the injectable botulinum toxin formulations have a reduced tendency to diffuse after injection. In this way, certain preferred formulations of the invention permit more accurate delivery of botulinum toxin, dramatically reducing unwanted side effects associated with uncontrolled local diffusion of botulinum toxin.

This example reports a comparative study of the tendency of botulinum toxin in various formulations to diffuse following injection. The study involved three botulinum toxin formulations: (1) BOTOX®; (2) RT003, a buffered and stabilized solution containing the 150 kD type A botulinum toxin molecule non-covalently associated with a positively charged carrier having the formula RKKRRQRRRG-(K)$_{15}$-GRKKRRQRRR; and (3) RTT150, which is identical to the RT003 formulation, except that is does not contain the positively charged carrier present in RT003.

Figure 2:
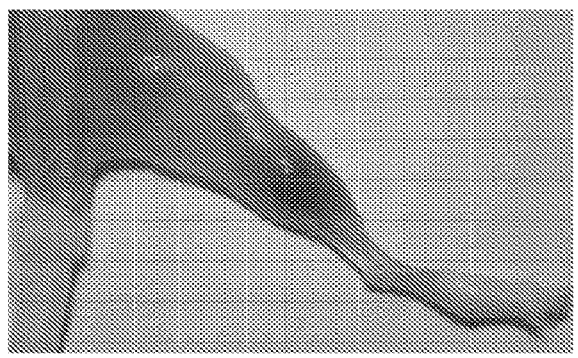
FIG. 2.
Figure 2:
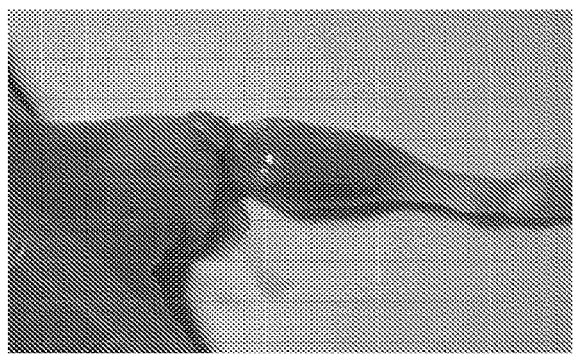

The gastrocnemius muscle of each of the mice used in the study was injected with one of the aforementioned botulinum toxin formulations, either at the lateral-to-midline portion of the muscle (FIG. 2A), or at the midline portion of the muscle (FIG. 2B). DAS assays were performed on each of the mice for four days after injection with the botulinum toxin to determine whether the botulinum toxin of the respective formulation exhibited any tendency to diffuse from the gastrocnemius muscle toward the hind paws of the mouse. From the DAS assays, any decreased ability of the test animals to abduct their hind digits was interpreted as an indication of botulinum toxin diffusion.

Figure 3:
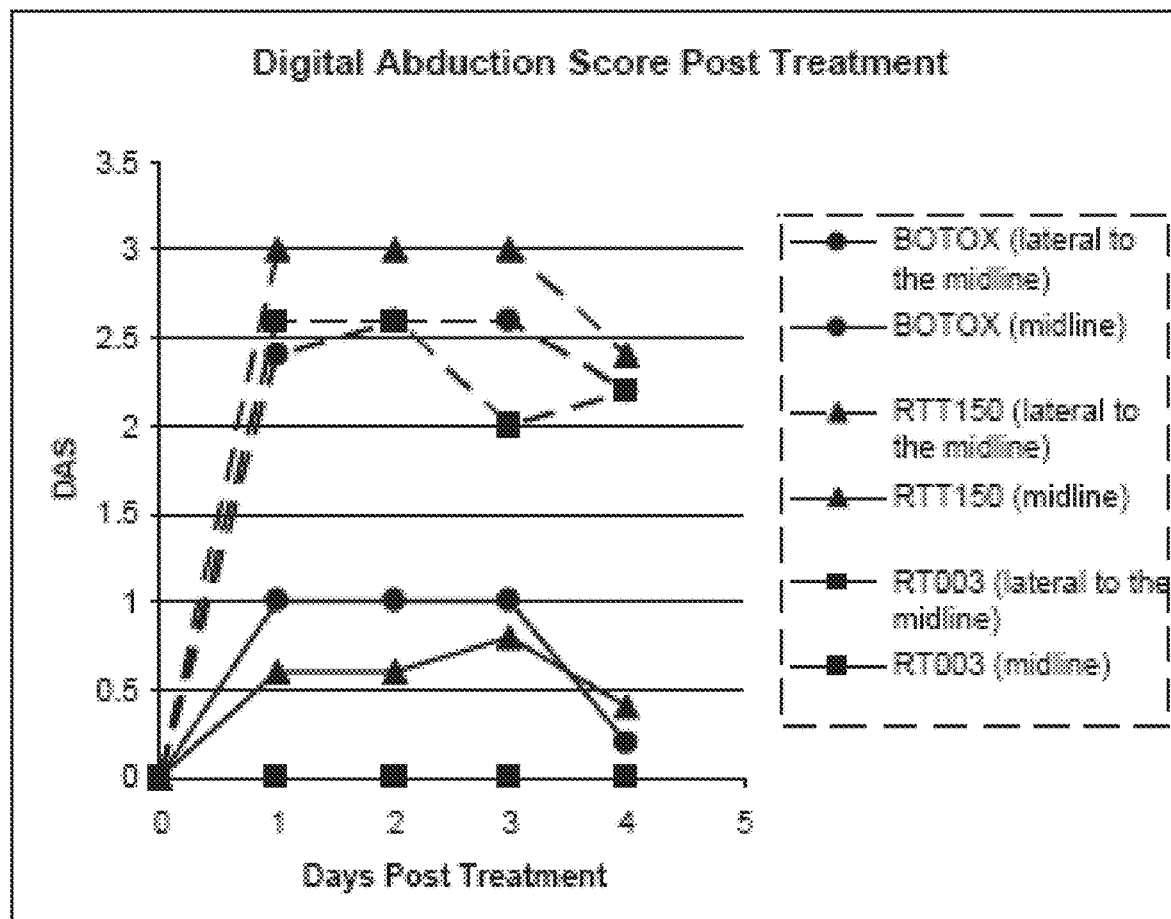
FIG. 3: Digital abduction scores measured as a function of time following injection of RT003, RTT150, or BOTOX® into either the lateral-to-midline or midline portion of the gastrocnemius muscle of a mouse.

FIG. 3 shows the results of the DAS assays performed after injecting the test animals with the different botulinum toxin formulations as described above. Note that the digital abduction scores are grouped into two clusters, corresponding to whether the injection was at the midline or the lateral-to-midline portion of the gastrocnemius muscle. The generally lower DAS scores for midline injections, as compared to DAS scores for lateral-to-midline injections, indicates that the degree of paralysis in the hind paws of the test animals is generally less following midline injection. Without wishing to be limited by theory, it is believed that this behavior results from the greater distance that botulinum toxin has to travel to reach the hind digits of a test animal following midline injection, as compared to lateral-to-midline injection. This greater required distance of travel by the botulinum toxin is believed to decrease the likelihood of paralysis of the hind digits.

FIG. 3 shows a digital abduction score of zero for all four days following midline injection of the RT003 formulation. This result indicates that the botulinum toxin in the RT003 formulation stays localized in the midline portion of the gastrocnemius muscle upon injection and that no paralysis-causing diffusion occurs on the timescale of the experiment. By contrast, digital abduction scores above the 0.4 DAS baseline are observed following injection of the RTT150 and BOTOX® formulations, with the average DAS score being higher for the BOTOX® formulation. The DAS results for the RTT150 and BOTOX® formulations indicate that hind digit paralysis of the test animals was observed after midline injection of these formulations, with a greater degree of paralysis observed after the injection of the BOTOX® formulation. These data suggest that the botulinum toxin molecules in the RTT150 and BOTOX® formulations are capable of locally diffusing after injection, with a greater degree of local diffusion for the botulinum toxin molecules in the BOTOX® formulation.

FIG. 3 also shows that hind digit paralysis is observed for all test animals following lateral-to-midline injection, irrespective of the specific botulinum toxin formulation. As discussed above, this greater degree of paralysis following lateral-to-midline injection, as compared to midline injection, is believed to relate to a shorter travel distance for the botulinum toxin to the hind paws of the test animals. However, while all three botulinum toxin formulations exhibit paralysis-causing diffusion following lateral-to-midline injection, the degree of paralysis in test animals injected with RT003 is less, on average, than the degree of paralysis observed for the RTT150 and BOTOX® formulations during the timescale of the experiment. Thus, the DAS assay data corresponding to lateral-to-midline injection is qualitatively similar to that for midline injection in that it shows a decreased tendency for local diffusion of botulinum toxin for the RT003 formulation, as compared to RTT150 and BOTOX®.

A comparison of the local diffusion rate following midline injection and lateral-to-midline injection can be made by considering a parameter called the "diffusion index", which is defined according to Equation (1):

$$\text{diffusion index} = \frac{\text{midline digital abduction score}}{\text{lateral-to-midline digital abduction score}} \times 100. \quad (1)$$

Since digital abduction scores can range from 0 to 4, and lateral-to-midline digital abduction scores are expected to be higher than midline digital abduction scores (as discussed above), diffusion index values will typically range from 0 to 100. A diffusion index value that approaches 100 indicates that the ratio of the midline and lateral-to-midline digital abduction scores approaches unity. This may occur if the rates of diffusion following injection are sufficiently high that the diffusion times for the botulinum toxin to reach and to paralyze the hind digits of the test animal following midline and lateral-to-midline injection are comparable or nearly the same. At the other extreme, diffusion index values that approach zero indicate that the ratio of the midline and lateral-to-midline digital abduction scores is approaching zero. This may occur if diffusion of the botulinum toxin following midline injection is so low that it is insufficient to cause paralysis in the hind digits of the test animals, even though paralysis is observed following lateral-to-midline injection.

Table 1 shows diffusion index values calculated using digital abduction scores following midline or lateral-to-midline injection of BOTOX®, RT003, and RTT150, as reported in the experiment corresponding to FIG. 3. On the timescale of the experiment, the diffusion index values corresponding to injection of the BOTOX® formulation are higher than the values observed for the RTT150 and RT003 formulations. This indicates that, for injection of the BOTOX® formulation, the ratio of the midline and lateral-to-midline digital abduction scores are closer to unity, compared to the ratios observed for the RTT150 and RT003 formulations. Since botulinum toxin must diffuse further to cause hind-digit paralysis of a test animal following midline injection, the observation that the ratio of the midline and lateral-to-midline digital abduction scores following BOTOX® injection is closer to unity suggests that the botulinum toxin diffusion rate following midline injection of BOTOX® is fairly substantial relative to the rate following lateral-to-midline injection. In other words, the increased diffusion path length associated with midline injection is less of a barrier to causing hind-digit paralysis.

In contrast, the diffusion index values for RT003 are all zero on the four-day timescale of the experiment. This result indicates that no paralysis-inducing diffusion is observed following midline injection of RT003. In other words, the RT003 formulation, which contains the type A botulinum toxin molecule non-covalently associated with a positively charged carrier, permits enhanced localization injected type A botulinum toxin. In this way, the RT003 formulation affords an improved safety profile compared to that of the BOTOX® formulation and minimizes unwanted paralysis.

The observed diffusion index values for RTT150, while not zero as in the case of RT003, are still less than those observed for the BOTOX® formulation [see Table 1]. This result indicates that enough botulinum toxin diffusion occurs to produce observable hind digit paralysis on the four-day timescale of the experiment, but that the time required for paralysis-causing diffusion of botulinum toxin is relatively longer following midline injection.

TABLE 1

Botulinum toxin diffusion index measurements
for RTT150, BOTOX ® and RT003.

| | Days Post Treatment | | | | |
|---|---|---|---|---|---|
| | 0 | 1 | 2 | 3 | 4 |
| BOTOX ® | NA | 42 | 38 | 38 | 9 |
| RT003 | NA | 0 | 0 | 0 | 0 |
| RTT150 | NA | 20 | 20 | 27 | 17 |

Example 3

Injectable Botulinum Toxin Formulations with Reduced Tendency to Generate Antibodies When botulinum toxin is periodically injected into a patient to treat an unwanted condition such as wrinkles, it is often observed that efficacy of the botulinum toxin decreases with successive injections, even though the duration of the effects of the botulinum toxin may remain the same. This phenomenon is believed to be the result of the formation of antibodies to the botulinum toxin by the immune system of the patient. From a treatment perspective, the formation of antibodies to botulinum toxin by the patient is undesirable, because increasingly larger doses of botulinum toxin are then required to achieve the same effect, which presents serious issues related to both safety and cost.

In certain embodiments, this invention provides injectable botulinum toxin formulations that have a decreased tendency to induce antibody formation, as compared to currently available commercial injectable botulinum toxin formulations. Thus, in these embodiments, botulinum toxin formulations help to minimize the risk associated with botulinum toxin injection by permitting one, over time, to use less toxin to achieve the same effect.

In this example, the DAS assay data obtained after repeated RT003 and BOTOX® injections as described in Example 2 are analyzed as a function of time to determine how the efficacy of these two formulations changes upon repeated administration to the same test animals. Generally, after repeated administration of either formulation, the duration of effects associated with botulinum toxin were the same. However, the degree of muscle paralysis upon repeated administration varied depending on the formulation. To quantify the change in the degree of muscle paralysis, the percent change in the digital abduction scores following injection of either RT003 or BOTOX® was determined according to Equation (2):

$$\% \text{ change in } DAS = \frac{DAS \text{ for } nth \text{ treatment} - DAS \text{ for first treatment}}{DAS \text{ for first treatment}} \times 100\% \quad (2)$$

Since the numerator of Equation (2) is the difference between the measured digital abduction scores for the $n^{th}$ and the first treatment, the percent change in DAS will be negative if the digital abduction score measured for the $n^{th}$ treatment is less than the digital abduction score measured for the first treatment. In other words, the percent change in DAS is negative when less paralysis is observed after the nth treatment, as compared to the first treatment. Table 2 shows the percent change in the measured DAS values following repeated administration of RT003 and BOTOX® formulations according to the procedure described in Example 2.

TABLE 2

Percent Change in DAS Value after Repeated Administration
of RT003 and BOTOX ®

| | 1st treatment | 1st retreatment | 2nd retreatment |
|---|---|---|---|
| RT003 | 0% | 0% | −30% |
| BOTOX ® | 0% | −44% | −67% |

As indicated in Table 2, after the first retreatment, the percent change in the digital abduction score was −44% for the BOTOX® formulation, which suggests a substantial drop in the efficacy. In contrast, the percent change in the digital abduction score for the RT003 formulation was zero, indicating that the DAS score after the second retreatment was the same as after the initial administration and first retreatment. This result indicates that the degree of paralysis observed after the first retreatment of RT003 is the same as the degree of paralysis following the first treatment and that negligible formation of neutralizing antibodies occurred in the test animals even after the first retreatment. After the 2nd retreatment of RT003 and BOTOX®, the calculated percent changes in DAS values were negative for both formulations, although the magnitude of the percent change in DAS values for the RT003 formulation was half of the value determined for BOTOX®. The larger and negative percent change in DAS values observed for BOTOX® suggest that the test animals had a higher rate of antibody generation to BOTOX®, as compared to RT003. Thus, these data indicate that formulations contemplated by this invention, such as RT003, may have a lower tendency to induce the formation of antibodies that neutralize the effect of botulinum toxin. Accordingly, this result suggests that by using formulations contemplated by this invention, one can, over time, use less botulinum toxin to achieve the same therapeutic effect.

Example 4

Injectable Botulinum Toxin Formulations with Improved Stability

This example demonstrates that the positively charged carrier molecules used in the injectable botulinum toxin formulations of the invention not only enhance the safety profile of the formulations (Example 2), but also improve their stability. Table 3 shows the results of aging experiments wherein the RT003 and RTT150 formulations are aged at 4° C. (RT003 only) and at 40° C. (both RT003 and RTT150) for various time intervals. After aging at the specified temperatures for the specified times, the potency of the RT003 and RTT150 formulations were measured via a series of mouse IP LD50 assays. The results, summarized in Table 3, indicate that the potency of RT003 is essentially unchanged following aging at 4° C., even after six months. Furthermore, the potency of the RT003 formulation, as measured by the formulation's ability to kill the target animals in a mouse IP LD50 assay, decreases only slightly even if the RT003 formulation is aged at elevated temperature (40° C.) for six months. By contrast, the RTT150 formulation exhibited a significant decrease in potency following only one month of aging at 40° C. Since the RT003 and RTT150 formulations are identical, with the exception that the RT003 formulation also contains a positively charged carrier molecule having the formula RKKRRQRRRG-(K)$_{15}$-GRKKRRQRRR, these data indicate that the positively charged carrier molecule improves the stability of the botulinum toxin in the RT003 formulation.

TABLE 3

Results of Mouse IP LD50 Assays following Aging of RT003 and RTT150 At Various Conditions

| | Condition (° C.) | Time (months) | % Target |
|---|---|---|---|
| RT003 | 4 | 0 | 100% |
| | 4 | 6 | 118% |
| | 40 | 6 | 93% |
| RTT150 | 40 | 1 | <50% |

---

What is claimed is:

1. A sterile injectable composition comprising
a protein consisting of a botulinum toxin complex, a reduced botulinum toxin complex, or a botulinum toxin; and
a positively charged carrier with the amino acid sequence RKKRRQRRRG-(K)$_{15}$-GRKKRRQRRR (SEQ ID NO: 5);
  wherein the botulinum toxin component non-covalently associates with the positively charged carrier, and
  wherein the composition is formulated for injection and has a viscosity in the range of about 0.4 to about 2.0 cP.

2. The sterile injectable composition of claim 1, wherein the botulinum toxin component is a 150 kD Type A botulinum toxin.

3. The sterile injectable composition according to claim 1, wherein the botulinum toxin component is obtained from serotype A of *C. botulinum*.

4. The sterile injectable composition according to claim 1, wherein the positively charged carrier stabilizes botulinum toxin against degradation.

5. The sterile injectable composition according to claim 1, wherein the positively charged carrier reduces local diffusion of botulinum toxin following injection.

6. A syringe comprising a composition comprising
a protein consisting of a botulinum toxin complex, a reduced botulinum toxin complex, or a botulinum toxin; and
a positively charged carrier with the amino acid sequence RKKRRQRRRG-(K)$_{15}$-GRKKRRQRRR (SEQ ID NO: 5);
  wherein the composition comprises an effective amount of the botulinum toxin component and the botulinum toxin component non-covalently associates with the positively charged carrier, wherein the composition is disposed in the syringe and formulated for injection.

7. The syringe of claim 6, wherein the botulinum toxin component is a 150 kD Type A botulinum toxin.

8. The syringe of claim 6, wherein the composition comprises 50 U to 200 U of botulinum toxin.

9. The syringe according to claim 6, wherein the botulinum toxin component is obtained from serotype A of *C. botulinum*.

10. The syringe according to claim 6, wherein the positively charged carrier stabilizes botulinum toxin against degradation.

11. The syringe according to claim 6, wherein the positively charged carrier reduces local diffusion of the botulinum toxin following injection.

12. A reconstituted botulinum toxin composition comprising
a protein consisting of a botulinum toxin complex, a reduced botulinum toxin complex, or a botulinum toxin; and
a positively charged carrier with the amino acid sequence RKKRRQRRRG-(K)$_{15}$-GRKKRRQRRR (SEQ ID NO: 5); and
a pharmaceutically acceptable aqueous liquid diluent,
  wherein the botulinum toxin component non-covalently associates with the positively charged carrier,
  wherein the composition is formulated for injection, and
  wherein the reconstituted botulinum toxin composition has a viscosity in the range of about 0.4 to about 2.0 cP.

13. The reconstituted botulinum toxin composition of claim 12, wherein the composition comprises 50 U to 200 U of botulinum toxin.

* * * * *